United States Patent [19]

DiMarchi et al.

[11] Patent Number: 4,732,971

[45] Date of Patent: Mar. 22, 1988

[54] SYNTHETIC VACCINES FOR FOOT AND MOUTH DISEASE

[75] Inventors: Richard D. DiMarchi, Carmel; Gerald S. Brooke, Indianapolis, both of Ind.

[73] Assignee: Eli Lilly and Company, Indianapolis, Ind.

[21] Appl. No.: 864,186

[22] Filed: May 16, 1986

Related U.S. Application Data

[63] Continuation-in-part of Ser. No. 740,780, Jun. 3, 1985, abandoned.

[51] Int. Cl.$^4$ .......................... C07K 7/10; A61K 39/00
[52] U.S. Cl. ........................................ 530/324; 424/88
[58] Field of Search ........................... 530/324; 424/88

[56] References Cited

U.S. PATENT DOCUMENTS 4,140,763 2/1979 Bachrach et al. ..................... 424/89
4,605,512 8/1986 Schaller et al. ...................... 530/326

OTHER PUBLICATIONS

Bachrach et al., *J. Immunol.,* 115, 1636–1641, (1975).
Kleid et al., *Science,* 214, 1125–1129, (1981).
Bittle et al., *Nature,* 298, 30–33, (1982).
Strohmaier et al., *J. Gen. Virol.,* 59, 295–306, (1982).
Clarke et al., *FEBS Letters,* 157, 261–264, (1983).
Brown, *Biotechnology,* 3, 445–448, (1985).

*Primary Examiner*—Delbert R. Phillips
*Attorney, Agent, or Firm*—William C. Martens; Leroy Whitaker

[57] ABSTRACT

A class of compounds having activity in treating and/or preventing foot and mouth disease is disclosed. The compounds contain a sequence of the formula

X-A-Y-B-Z in which A and B are amino acid residue sequences comprising sequences of the foot-and-mouth disease virus $VP_1$ capsid protein serotypes, one of which contains from 18 to 24 amino acid residues and includes the amino acid residue sequence in positions 141 to 158 of the O serotype or the equivalent sequence of other serotypes and the other of which contains from 14 to 20 amino acid residues and includes the amino acid residue sequence in positions 200 to 213 of the O serotype or the equivalent sequence of other serotypes;

X is H, H-Cys, or H-Cys-Cys, the sulfhydryls of which may be blocked or free;

Z is OH, Cys-OH, or Pro-Cys-Gly-OH, the sulfhydryls of which may be blocked or free; and Y is a sequence of from about 2 to about 6 amino acid residues.

21 Claims, No Drawings

SYNTHETIC VACCINES FOR FOOT AND MOUTH DISEASE

CROSS-REFERENCE

This application is a continuation-in-part of application Ser. No. 740,780 filed June 3, 1985, now abandoned.

BACKGROUND OF THE INVENTION

Foot-and-mouth disease (FMD) is a highly contagious, debilitating disease that afflicts cloven-hoofed animals. The causative agent, foot-and-mouth disease virus (FMDV), is a small animal virus of the picornavirus family having a single stranded positive sense RNA genome of about 8000 nucleotides.

In the past, vaccines have been produced for FMD using either an inactivated virus or a live attenuated virus. These approaches, although generally effective, have not been problem-free. Occasions in which the virus was incompletely inactivated or insufficiently attenuated can and have given rise to FMD outbreaks. A synthetic FMDV vaccine which would eliminate all aspects of virus handling in production and vaccination is perceived as a most desirable alternative [D. Rowlands, Endeavor 8 (3), 123-127 (1984)].

Studies of FMDV over the last several years have established that the picornavirus contains primarily four capsid proteins designated $VP_1$, $VP_2$, $VP_3$, and $VP_4$. The actual labelling of these VP proteins has been subject to a measure of inconsistency. The relevant protein insofar as this invention is concerned has been designated $VP_3$ by some research groups [see, e.g., Kleid et al., Science 214, 1125 (1981)] while being labelled $VP_1$ by others [see, e.g., Clarke et al, FEBS Letters 157, 261 (1983)]. For purposes herein, this protein is designated $VP_1$.

$VP_1$ has been the subject of considerable investigation and structural analysis, it having been found to elicit a neutralizing antibody response in swine [J. Laporte, J. Grosclaude, J. Wantyghem, S. Bernard, P. Rouze, C. R. Acad. Sci. 276, 3399 (1973)] and to protect both swine and cattle from FMDV infection [H. L. Bachrach, D. M. Moore, P. D. McKercher, J. Polatnick, J. Immunol. 115, 1636 (1975)]. A biosynthetic fusion polypeptide of TrpLE and $VP_1$ upon multiple vaccination has been reported to protect cattle and swine against a viral contact challenge [D. G. Kleid, D. Yansura, B. Small, D. Dowbenko, D. Moore, M. Grubman, P. McKercher D. O. Morgan, E. V. Robertson, H. L. Bachrach, Science 214, 1125-1129 (1981).

Strohmaier et al., J. Gen. Virol. 59, 295-306 (1982), by chemical and enzymatic digestion of $VP_1$, have concluded that major immunogenic regions capable of raising neutralizing antibodies are present at amino acid sequences 146-154 and 201-213.

Bittle et al., Nature 298, 30-33 (1982) chemically synthesized peptides corresponding to regions 141-160 and 200-213 of the $VP_1$ polypeptide of FMDV and demonstrated the ability of these peptides to produce high levels of neutralizing antibody in guinea pigs and rabbits. A report on this work is also contained in the PCT International patent application No. WO 83 03,547, published Oct. 27, 1983.

A major theme which runs throughout all of the foregoing work with the small peptide sequences is the belief and finding that their immunogenic effect, if present at all, is achieved only upon the linking of the peptide to a high molecular weight carrier, most often keyhole limpet hemocyanin (KLH) carrier.

The aforementioned PCT application No. WO 83 03,547 appears to suggest the converse. In fact, the data presented in the publication establish that a small peptide, in monomeric and uncyclized form, is incapable of eliciting a neutralizing index sufficient to achieve viral protection. Specifically, the publication states that a neutralizing index of about 1.5 or greater is required to protect an animal against the virus and that the neutralizing index of the monomeric, unconjugated peptide having a sequence which corresponds substantially to the amino acid residue sequence in positions about 141 to about 160 of O1K FMDV is approximately 0.5. This result is to be compared with neutralizing indices of about 3.7 to about 3.9 reported for the same peptide when conjugated to KLH.

A class of novel, monomeric, unconjugated, small peptides has now been discovered. These peptides, administered free of any carrier, are capable of eliciting an unforeseen markedly enhanced neutralization response against FMDV. These peptides have induced unprecedented protection in cattle with single vaccination and complete protection after repeat immunization. Until the present discovery, this latter achievement has been proven only with antigens approximately five times larger in size than these newly discovered peptides.

SUMMARY OF THE INVENTION

Thus, this invention is directed to a compound containing a sequence of the formula
ti X-A-Y-B-Z in which A and B are amino acid residue sequences comprising sequences of the foot-and-mouth disease virus $VP_1$ capsid protein serotypes, one of which contains from 18 to 24 amino acid residues and includes the amino acid residue sequence in positions 141 to 158 of the O serotype or the equivalent sequence of other serotypes and the other of which contains from 14 to 20 amino acid residues and includes the amino acid residue sequence in positions 200 to 213 of the O serotype or the equivalent sequence of other serotypes;

X is H, H-Cys, or H-Cys-Cys, the sulfhydryls of which may be blocked or free;

Z is OH, Cys-OH, or Pro-Cys-Gly-OH, the sulfhydryls of which may be blocked or free; and Y is a sequence of from about 2 to about 6 amino acid residues.

DETAILED DESCRIPTION OF THE INVENTION

As noted, this invention is directed to a class of synthetic, immunogenic peptides having the formula

X-A-Y-B-Z.

The groups A and B represent amino acid sequences corresponding to selected sequences present in the $VP_1$ capsid protein of FMDV serotype O, subtype 1, strain Kaufbeuren ($O_1K$) and equivalent analogous sequences present in any of other foot-and-mouth disease virus serotypes.

Seven serotypes of FMDV are known to exist. The most common are European and carry designations A, O, and C. Others are three South African, SAT-1, SAT-2, and SAT-3, and one Asian, Asia-1. Each serotype in addition is known to have a number of subtypes and associated subtype strains. Specific examples are serotype O, subtype 1, strain Kaufbeuren (O₁K); serotype O, subtype 1, strain Campos (O₁C); serotype O, subtype 1, strain British Field Strain (O₁BFS); serotype A, subtype 10, strain 61 (A10,61); serotype A, subtype 12, strain 119 (A12,119); serotype A, subtype 24, strain Cruzeiro (A24C); serotype A, subtype 27 (A27); serotype A, subtype 79 (A79); and serotype C, subtype 3, strain Indaial (C3I).

The amino acid residue sequences in positions 141-158 and 200-213 of the O serotype represent the focus of the definitions of groups A and B of the peptides of this invention. In any specific instance group A includes one of the sequences and group B the other. In addition, the analogous but not necessarily identical sequences present in any of the other serotype and serotype subtypes are included within the definition of the groups A and B as used herein.

For purposes of illustration, the following are provided as examples of the sequence 141-158 for O₁K and analogous sequences of other viral serotypes and subtypes:

|        | 141 | | | 150 | | | 158 |
|--------|-----|---|---|-----|---|---|-----|
| O₁K    | ValProAsnLeuArgGlyAspLeuGlnValLeuAlaGlnLys ValAlaArgThr |
| O₁BFS  | ValProAsnLeuArgGlyAspLeuGlnValLeuAlaGlnLys ValAlaArgThr |
| O₁C    | ValProAsnValArgGlyAspLeuGlnValLeuAlaGlnLys ValAlaArgThr |
| A10,61 | Ser — ArgSer — GlyAspLeuGlySer Ile AlaAlaArgValAlaThrGln |
| A12,119| SerGly — Val ArgGlyAspPheGlySer LeuAlaProArgValAlaArgGln |
| A24C   | SerGly — ArgArgGlyAspMetGlyThrLeuAlaAla ArgValValLys Gln |
| A27    | Gln — — ArgAla GlyAspMetGlySer LeuAlaAla ArgValAlaLys Gln |
| A79    | SerGly — ArgArgGlyAspMetGlySer LeuAlaAla ArgValAlaLys Gln |
| C3I    | — — — ArgArgGlyAspLeuValHis LeuAlaAla Ala His AlaArgHis |

The following are examples of the sequence 200-213 for O₁K and analogous sequences of other viral serotypes and subtypes:

|        | 200 | 213 |
|--------|-----|-----|
| O₁K    | ArgHis LysGlnLys Ile ValAlaProVal LysGlnThrLeu |
| O₁BFS  | ArgHis LysGlnLys Ile ValAlaProVal LysGlnThrLeu |
| A10,61 | ArgTyrLysGlnLys Ile Ile AlaProAla LysGlnLeuLeu |
| A12,119| ArgHis LysGlnLys Ile Ile AlaProGlyLysGln — Leu |
| A24C   | ArgHis LysGlnLys Ile Ile AlaProAla LysGlnLeuLeu |
| C3I    | ArgHis LysGlnProLeu Ile AlaProAla LysGlnLeuLeu |

In the peptides of this invention, one of the groups A and B contains a peptide sequence 141-158 and the other a peptide sequence 200-213. Preferably, one of the groups A and B is a peptide sequence 141-158 and the other is a peptide sequence 200-213. More preferably, group A is the sequence 200-213 and group B the sequence 141-158. Even more preferably, the groups A and B of the peptides of this invention are peptide sequences derived from the same FMDV serotype.

The group X represents the amino terminal portion of the peptides of this invention. X can represent the hydrogen of the amino terminus or a mono-cysteinyl or di-cysteinyl extension. If X is mono- or di-cysteinyl, the cysteine sulfhydryls may be blocked or free. Any of a wide range of routine blocking groups can be used. Examples of these are sulfonate, carboxymethyl, carboxamidomethyl, aminoethyl, and the like. Preferably, X is hydrogen.

The group Z defines the carboxyl terminal of the peptides of this invention. Z thus is a hydroxyl or a cysteine-containing extension, viz., cysteine or the tripeptide Pro-Cys-Gly-OH. Again, the cysteine may be blocked or free, and, if blocked, can be so blocked using any of the same blocking groups as hereinbefore described.

The group Y links groups A and B and represents an amino acid residue or a sequence having from 2 to 6 amino acid residues. Preferably, Y is an amino acid sequence having from 2 to 4 amino acid residues. The sequence can be comprised of any of a wide range of amino acid residues, proline being an amino acid residue of choice, and sequences containing Pro-Pro being particularly preferred. A specific such sequence is Pro-Pro-Ser.

Included in the compounds of this invention are their pharmaceutically acceptable non-toxic acid addition salts and their pharmaceutically acceptable non-toxic carboxylic acid salts.

The term "pharmaceutically acceptable non-toxic acid addition salts" encompasses both organic and inorganic acid addition salts including, for example, those prepared from acids such as hydrochloric, hydrofluoric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like.

Preferably, the acid addition salts are those prepared from hydrochloric acid, acetic acid, or succinic acid. Any of the above salts is prepared by conventional methods.

The term "carboxylic acid salts" includes, for example, ammonium, alkali metal salts such as sodium, potassium, and lithium, and the like.

For the sake of convenience, the amino acids referred to herein are described by their approved shorthand three-letter designations.

These designations are as follows:

|               | 3-letter |
|---------------|----------|
| Alanine       | Ala      |
| Arginine      | Arg      |
| Asparagine    | Asn      |
| Aspartic Acid | Asp      |
| Cysteine      | Cys      |
| Glutamic Acid | Glu      |
| Glutamine     | Gln      |
| Glycine       | Gly      |
| Histidine     | His      |
| Isoleucine    | Ile      |
| Leucine       | Leu      |
| Lysine        | Lys      |
| Phenylalanine | Phe      |
| Proline       | Pro      |
| Serine        | Ser      |
| Threonine     | Thr      |
| Tryptophan    | Trp      |
| Tyrosine      | Tyr      |
| Valine        | Val      |

Examples of compounds of this invention are:

VP₁(O₁K)   H[(200-213)ProProSer(141-158)]ProCysGly—OH;

-continued

| | |
|---|---|
| VP$_1$(O$_1$K) | H—Cys[(200-213)ProProSer(141-158)]Cys—OH; |
| VP$_1$(O$_1$K) | H—CysCys[(200-213)ProProSer(141-158)]ProCysGly—OH; |
| VP$_1$(O$_1$K) | H[(200-213)ProProSer(141-158)]OH; |
| VP$_1$(O$_1$BFS) | H[(141-158)ProPro(200-213)]OH; |
| VP$_1$(A$_{10,61}$) | H[(141-158)LeuProProSer(200-213)]OH; |
| VP$_1$(A$_{12,119}$) | H—Cys[(200-213)LeuProProSer(141-158)]OH; |
| VP$_1$(A$_{24}$C) | H[(200-213)ValProProThrArg(141-158)]OH; |
| VP$_1$(O$_1$C) | H—CysCys[(141-158)ProPro(200-213)]Cys—OH; |
| VP$_1$(C$_3$I) | H[(200-213)ProProSer(141-158)]OH; |
| | and the like. |

The compounds of this invention can be prepared by any of a variety of recognized peptide synthesis techniques including classical (solution) methods, solid phase methods, and the more recently available recombinant DNA methods.

One of the principal methods for preparing the compounds of this invention is by the solid phase technique in which the amino acid sequence is constructed sequentially from an initial, insoluble, resin-supported C-terminal amino acid. Techniques for the solid phase method are described by J. Stewart et al., *Solid Phase Peptide Synthesis*, Pierce Chemical Co., Rockford, Ill., 1984.

Specific examples in state of the art solid phase peptide synthesis which may be utilized in the preparation of these FMDV synthetic immunogens are provided in reports by R. D. DiMarchi, J. P. Tam, R. B. Merrifield, *Int. J. Pep. Prpt. Res.* 19, 270-279 (1982); R. B. Merrifield, L. D. Vizioli, H. G. Boman, *Biochem.* 21, 5020-5031 (1982); S. Mojsov, R. B. Merrifield, *Eur. J. Biochem.* 145, 601-605 (1984). The more improtant features are the following:

1. Utilization of copoly(styrene—1% divinylbenzene) resin, 200-400 mesh beads, available from Bio-Rad laboratories.
2. Functionalization of the resin support to aminomethyl-resin by the method of Mitchell et al., 1978.
3. Amidation of the carboxy-terminal amino acid to the aminomethyl-resin as its t-butyloxycarbonyl-aminoacyl-[4-(oxymethyl)phenyl] acetic acid derivative.
4. Cleavage of the amino-protecting t-butyloxycarbonyl (Boc) group in 50% TFA/CH$_2$Cl$_2$ and neutralization of the amine in 5% DIEA/CH$_2$Cl$_2$.
5. Double coupling at each residue is utilized. With the exception of Asn, Gln, and Arg the first coupling is by preformed symmetrical anhydride. The second coupling in all cases is by preformed HOBt-ester. The first coupling for the aforementioned exceptions is analogous to the second coupling.
6. The peptide is cleaved from the resin support by exposure to 90% anhydrous HF/10% p-cresol at 0° C. for 60 minutes.
7. The following side-chain protecting groups preferably are utilized: Arginine (tosyl), Aspartic acid (O-cyclopentyl), Cysteine (4-methoxybenzyl), Glutamic acid (O-cyclopentyl), Histidine (benzyloxymethyl), Lysine (2-chlorobenzyloxycarbonyl), Serine (benzyl), Threonine (benzyl), Tryptophan (formyl) and Tyrosine (2-bromobenzyloxycarbonyl).

Compounds of this invention can also be prepared via recombinant DNA methodology. In their preparation, a nucleotide sequence coding for the desired peptide is prepared using now routine methods for such synthesis. These methods generally involve preparation of oligonucleotides coding both for fragments of the desired coding sequence and for the complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the peptide product for which it codes to be expressed. A suitable cloning vector contains at least a portion of a gene's expression control sequence.

A typical expression control sequence can be described in terms of five elements. In the order in which they appear in the gene, the elements are as follows: (a) the promoter region; (b) the 5' un-translated region; (c) the protein coding sequence; (d) the 3' untranslated region; and (e) the transcription termination site.

The function of each of these elements in gene system is well recognized. The promoter region mediates initiation of messenger RNA (mRNA) production (transcription). The promoter may be (1) free of external control (constitutive), (2) under the control of a repressor, a substance that, when present, represses gene function, or (3) under the control of an inducer, a substance that is required to induce gene function. The lipoprotein (lpp) gene, for example, is free from external control and thus is termed "constitutive".

Located at or near the promoter is the "transcription initiation site", a point at which RNA polymerase binds to initiate transcription of mRNA. Once transcription is initiated, mRNA is produced. The structure of the resulting mRNA is determined by the DNA sequences of the gene elements (b) to (d) above.

The resulting mRNA carries a sequence which is translatable into protein product. The translatable sequence is located downstream from the 5' untranslated region and upstream from the 3' untranslated region. Translation is mediated by the binding of ribosomes to a sequence in the mRNA 5' untranslated region denoted as the ribosome binding site and is initiated at the translation start codon (AUG) appearing as the first codon of the product gene sequence and coding as well for the amino acid methionine (Met). Translation terminates at one or more termination codons appearing at the end of the translation region.

By the techniques of recombinant DNA, it has become possible to prepare cloning vectors useful for the production of selected foreign (exogenous) proteins by inserting into such vectors an expression control sequence, i.e., a sequence of nucleotides that controls and regulates expression of structural genes with production of exogenous protein when operatively linked to those genes.

In the context of the foregoing, the term "expression control sequence" includes elements (a), (b), (d), and (e) above.

Recombinant DNA methodology can be employed to express compounds of this invention either as a portion of a larger "hybrid" molecule or by direct expression. In the direct expression mode, the cloning vector is designed such that the expression product is composed entirely of desired product preceded by a methionine (Met) residue resulting from the presence of the essential start codon. The superfluous Met residue can be removed by treating the product with cyanogen bromide or with phenyl isothiocyanate followed by a strong anhydrous acid, such as trifluoroacetic acid.

In the hybrid molecule expression mode, a DNA sequence coding for the desired product is inserted into the expression control sequence of a cloning vector at a point such that the product expressed comprises a hybrid protein. By "hybrid protein" as used herein is meant a recombinant DNA product comprising a foreign protein, generally all or a portion of the natural (endogenous) protein produced by the expression control sequence (for example, lipoprotein in the lipoprotein gene), to which is attached the desired protein.

The properly designed hybrid protein produced by recombinant DNA methodology will contain a cleavage site at the junction of the endogenous protein portion and the desired product. The cleavage site permits generation of mature product by chemical or enzymatic treatment of the hybrid protein product. Highly useful selective cleavage sites comprise a DNA sequence which codes for an amino acid or a sequence of amino acids which can be cleaved chemically or enzymatically at its C-terminal.

Examples of chemical agents useful for cleaving proteins are cyanogen bromide, BNPS-skatole, hydroxylamine, and the like Cyanogen bromide cleaves proteins at the C-terminal of a methionine residue. Therefore, the selective cleavage site is a methionine residue itself.

Hydroxylamine cleaves at the C-terminal of the moiety -Asn-Z- in which Z is Gly, Leu, or Ala.

BNPS-skatole cleaves at the C-terminal of a tryptophan residue.

Examples of enzylatic agents useful for cleavage are trypsin, papain, pepsin, plasmin, thrombin, enterokinase, and the like. Each effects cleavage at a particular amino acid sequence which it recognizes. For example, the selective cleavage site that enterokinase recognizes is the amino acid sequence -(Asp)$_n$-Lys- in which n is an integer from 2 to 4.

A most preferred selective cleavage site, especially for those compounds of this invention that lack methionine, is a methionine residue. This residue, joined to the N-terminus of the desired product, is readily cleaved by known methods using cyanogen bromide to produce the desired mature product.

In constructing useful cloning vectors, several elements are required. Two of the required elements are common to all useful cloning vectors. First, the vector must have a DNA segment containing a functional origin of replication (replicon). Plasmids and phage DNA by their very nature contain replicons facilitating replication in a host cell.

Secondly, the vector must have a DNA segment which conveys to a transformable host cell a property useful for selection of transformed cells from non-transformed cells. Any of a wide range of properties can be used for selection purposes. One of the most commonly used properties is antibiotic resistance, e.g., tetracycline resistance or ampicillin resistance.

The foregoing two elements generally are present in readily available and recognized cloning vectors. Examples of suitable cloning vectors are bacterial plasmids, such as plasmids from *E. coli*, including pBR322, pMB9, ColE1, pCR1; wider host range plasmids, including RP4; phage DNAs, such as lambda, and the like. Most, if not all, of the above recognized vectors already carry the aforedescribed two elements.

A third element is the expression control sequence. Any of a wide range of such control sequences can be used including, for example, those from the lipoprotein gene, the β-galactosidase gene, the tryptophan gene, the β-lactamase gene, phage lambda, and the like.

In producing a suitable cloning vector by insertion of the selected expression control sequence, routine methods are used. Various sites exist within cloning vectors at which cuts can be made using a restriction endonuclease specific for such site. Any of these sites can be selected for insertion of the expression control sequence. As an example, in the well-recognized and documented plasmid pBR322, several suitable restriction sites exist, any of which may be employed as insertion sites. A PstI site is located within the gene for β-lactamase. Other sites outside of any specific coding region are EcoRI and PvuII. These and other sites are well recognized by those skilled in the art.

Taking advantage of any of these sites or others, insertion of an expression control sequence or the essential portion thereof can be readily accomplished in production of vectors defined by this invention.

A fourth element, of course, is the DNA sequence coding for the desired product. As previously noted, this DNA sequence can be constructed synthetically, e.g., using the recognized phosphotriester method or other well-recognized methods.

Suitable cloning vectors can be used in a wide range of host organisms, for example, gram-negative prokaryotic organisms such as *Escherichia coli*, Serratia, Pseudomonas, and the like; gram-positive prokaryotic organisms, such as Bacillus, Streptomyces, and the like; and eukaryotic organisms, such as Saccharomyces, and the like. Preferably, the host organism is a gram-negative prokaryotic organism. Of gram-negative prokaryotic organisms, *E. coli* is especially preferred, for example, *E. coli* K-12 strains, such as RV308.

Employing well recognized methodology, the appropriately prepared cloning vectors are used to transform suitable host organisms, are amplified in such organisms, and exogenous protein product is expressed using standard fermentation conditions. The exogenous protein product is isolated by routine methods from the resulting fermentation broth.

The compounds of this invention, active in treating foot and mouth disease, can be used in a variety of pharmaceutical compositions and formulations and can be administered by a variety of conventional routes, such as intranasal, intramuscular, intravenous, subcutaneous, and intraperitoneal.

In administering the compounds of this invention, the pharmaceutical forms suitable for injection include sterile aqueous solutions or dispersions and sterile powders for reconstitution into sterile injectable solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, paraben, chlorobutanol, phenol, m-cresol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compounds of this invention in the required amount of the appropriate solvent with various of the other ingredients, as desired.

If desired, and for more effective distribution, the compounds can be incorporated into slow release or targeted delivery systems such as polymer matrices, liposomes, and microspheres.

Doses of the compounds of this invention are administered to the recipient for a period during which prophylactic or therapeutic treatment for foot and mouth disease is desired. The weight of the recipient and mode of administration will have an influence upon the size of the dose necessary to induce a particular response.

It is especially advantageous to formulate the compounds of this invention in unit dosage form for ease of administration and uniformity of dosage. Unit dosage form as used herein refers to a physically discrete unit suited to provide a single dose for the subject to be treated. Each unit contains a predetermined quantity of the compound calculated to produce the desired therapeutic or prophylactic effect in association with the pharmaceutically acceptable carrier. The specific unit dosage form is dictated by and directly dependent upon (a) the unique characteristics of the particular composition and (b) the particular effect to be achieved.

The following examples are illustrative of this invention. They are not intended to be limiting upon the scope thereof.

I. Preparation of Synthetic FMD Vaccines.

All peptides were synthesized through the use of the Beckman 990B solid phase peptide synthesizer, using semi-automated progamming. The initial functionalization, through the first amino acid loading, and all steps subsequent to the addition of the last amino acid, were achieved manually. All reagents unless otherwise stated were of the highest grade commercially available. Dimethylformamide (DMF) was stored over 4 Å molecular sieves for one week prior to use. Dichloromethane ($CH_2Cl_2$) was HPLC quality. Diisopropylethylamine (DIEA) was distilled from ninhydrin prior to use. Copoly(styrene-1% divinylbenzene) resin, 200–400 mesh beads, was purchased from Bio-Rad Laboratories. The quality of protected amino acids, purchased from Peninsula Laboratories and Bachem, was assessed by TLC, optical rotation, amino acid analysis and mass spectral analysis prior to use.

A. Preparation of Aminomethyl-resin

The preparation of aminomethyl-resin was as described by A. R. Mitchell, S. B. H. Kent, M. Engelhard, R. B. Merrifield, *J. Org. Chem.* 43, 2845–2852 (1978), with the exception that the desired funtionalization was four-times that reported. To 100 gm of thoroughly washed resin in a three-necked round bottom flask was added 16 gm (81 mmol) of N-(hydroxymethyl)phthalimide and 2 liters of trifluoroacetic acid/methylene chloride (1:1, v/v). Under rapid overhead stirring, trifluoromethanesulfonic acid (40 ml, 0.44 mol) was slowly added. After 6 hours of reaction at 22° C., the solution was filtered and washed extensively with 4 L each of trifluoroacetic acid/methylene chloride (1:1, v/v), methylene chloride, ethanol, and finally methylene chloride. The resin, once dried under vacuum, was refluxed for 16 hours in 2 liters of ethanol containing 5% hydrazine. The resin was filtered warm and washed with boiling ethanol (4×2 L), methanol (4×2 L), and methylene chloride (4×2 L). The product was dried under vacuum to yield an amine functionalization of 0.836 mmole/gm by ninhydrin analysis [V. Sarin, S. B. H. Kent, J. P. Tam, R. B. Merrifield, *Anal. Biochem.* 117, 147–151 (1981)].

B. Preparation of Boc-Glycine-[4(oxymethylphenyl)] acetic acid

The synthesis of Boc-glycine-[4(oxymethylphenyl)] acetic acid was exactly as described by J. P. Tam, S. B. H. Kent, T. W. Wong, R. B. Merrifield, *Synthesis,* 955–957 (1979), with a yield of 45%.

C. Attachment of Derivatized Glycine to Aminomethyl Resin.

Boc-Gly-[4(oxymethylphenyl)] acetic acid (1.4 mmol) was dissolved in 20 ml of DMF/methylene chloride (1:3, v/v) at 0° C. in the presence of 1.4 mmol of 1-hydroxybenzotriazole (HOBt) An equivalent amount (1.4 mmol) of dicyclohexylcarbodiimide (DCC) was added, and the reaction mixture was stirred for 10 minutes at 0° C., after which dicyclohexylurea was removed by filtration and the supernatant added to 4 gm of aminomethyl resin suspended in 20 ml of methylene chloride. After two hours, the resin was filtered, washed three times with 40 ml of methylene chloride, and then suspended in 40 ml of 0.5M acetic anhydride/0.1 M DIEA/methylene chloride. After an additional two hours, the resin was ninhydrin negative. The resin was washed three times with 40 ml of methylene chloride, and subsequently the t-butyloxycarbonyl protecting group of glycine was removed in 40 ml of trifluoroacetic acid/methylene chloride (1:1, v/v)

D. Repetitive Stepwise Synthetic Protocol

In each case double coupling of each amino acid, in three-fold excess to amine, was utilized. While Asn, Gln, and Arg were coupled twice as their preformed HOBt-esters, the remaining amino acids were first coupled as their preformed symmetrical anhydrides and repeated as their preformed HOBt-esters. Neutralization, deprotection and all washing were fully automated by the following protocol, at 15 ml of solvent/gram of starting resin.

| | |
|---|---|
| 1. | 5% DIEA/$CH_2Cl_2$ (2 × 2 minutes) |
| 2. | $CH_2Cl_2$ (6 × 1 minute) |
| 3. | First Coupling (1 × 120 minutes) |
| 4. | $CH_2Cl_2$ (6 × 1 minute) |
| 5. | 5% DIEA/$CH_2Cl_2$ (2 × 2 minutes) |
| 6. | $CH_2Cl_2$ (6 × 1 minute) |
| 7. | Second Coupling (1 × 120 minutes) |
| 8. | $CH_2Cl_2$ (6 × 1 minute) |
| 9. | 50% TFA/$CH_2Cl_2$ (1 × 2 minutes; 1 × 20 minutes) |
| 10. | $CH_2Cl_2$ (6 × 1 minutes) |

During the course of synthesis, aliquots of the resin were removed for preparation of shortened immunogens.

E. Preparation of $O_1K$, $VP_1$ (141–158)ProCysGly - [21 Residue Peptide].

Approximately three grams of peptidyl resin representing 1.34 gm of protected $O_1K$, $VP_1$ (141–158)-ProCysGly was treated with 30 ml of HF/p-cresol (9:1) at 0° C. for 60 minutes. Upon completion of cleavage the resin was evaporated to dryness under vacuum at 0° C. and subsequently washed with 5×50 ml of diethyl ether. The deprotected peptide was dissolved with successive acetic acid treatments 10% HOAc (3×30 ml), 50% HOAc (1×30 ml), and finally 10% HOAc (3×30 ml) The peptide was freeze dried to a yield of 76%. Ellman tritration revealed a minimum free sulfhydryl content of 70%. The peptide was purified by Sephadex G-25 gel permeation chromatography in 10% HOAc following dithiothreitol (DTT) reduction to yield a highly homogeneous monomeric fraction as assessed by analytical HPLC.

F. Preparation of $O_1K$, $VP_1$[LeuProProSer(141-158)] ProCysGly - - [25 Residue Peptide].

Approximately 1.1 gm of peptidyl resin representing 0.532 gm of protected $O_1K$, $VP_1$ [LeuProProSer(141–158)] ProCysGly was treated as in Part E to yield the desired peptide in 84% yield after DTT reduction/G-25 purification.

G. Preparation of $O_1K$, $VP_1$[(200–213)ProProSer(141–158)]ProCysGly - - [38 Residue Peptide].

Approximately 2.4 gm of peptidyl resin representing 1.29 gm of protected $O_1K$, $VP_1$ [(200–213)ProProSer(141–158)]ProCysGly was treated as in Part E to yield the desired peptide in 97% yield after DTT reduction/G-25 purification.

H. Preparation of $O_1K$, $VP_1$ [CysCys(200–213)ProProSer(141–158)]ProCysGly - - [40 Residue Peptide].

Approximately 2.5 gm of peptidyl resin representing 1.39 gm of protected $O_1K$, $VP_1$ [CysCys(200–213)-ProProSer (141–158)]ProCysGly was treated as in Part E to yield the desired peptide in 97% yield after DTT reduction/G-25 purification.

I. Preparation of $O_1K$, $VP_1$H-Cys-[ArqTyrAsnArgAsnAla(141–158)]LeuProProThr[GluAla (200–213)]OH - - [45 Residue Peptide].

Protected $O_1K$, $VP_1$ H-Cys-[ArgTyrAsnArgAsnAla(141–158)]LeuProProThr[GluAla(200–213)]-peptidyl resin was treated as in Part E to produce the title peptide.

The amino acid analysis of these five peptides is shown in Table 1 following.

TABLE 1

Amino Acid Composition of Synthetic FMDV Antigens

| | 21-Residue[a] | 25-Residue[a] | 38-Residue[a] | 40-Residue[b] | 45 Residue[h] |
|---|---|---|---|---|---|
| Lys | 1.09(1) | 1.12(1) | 3.68(4) | 3.74(4) | 3.99(4) |
| His | — | — | 0.91(1) | 0.90(1) | 1.13(1) |
| Arg | 2.00(2) | 1.99(2) | 2.69(3) | 2.88(3) | 4.45(5) |
| Asp | 1.08(1) | 1.94(2) | 2.19(2) | 2.09(2) | 3.78(4) |
| Thr | 1.05(1) | 1.04(1) | 2.09(2) | 2.27(2)[e] | 3.03(3) |
| Ser | — | 0.87(1) | 1.03(1) | 1.18(1)[e] | — |
| Glu | 2.08(2) | 2.13(2) | 4.18(4) | 4.14(4) | 5.22(5) |
| Pro | N.D.[c] | N.D.[c] | N.D.[c] | 5.16(5) | 4.46(4) |
| Gly | 2.07(2) | 2.12(2) | 2.27(2) | 2.38(2) | 1.22(1) |
| Ala | 2.14(2) | 2.17(2) | 3.22(3) | 2.99(3) | 5.12(5) |
| Cys | N.D.[d] | N.D.[d] | N.D.[d] | 2.52(3)[g] | N.D.[d] |
| Val | 2.91(3) | 2.98(3) | 4.83(5) | 5.20(5)[f] | 4.69(5) |
| Ile | — | — | 0.60(1) | 0.87(1)[f] | .73(1) |
| Leu | 2.82(3) | 3.97(4) | 4.34(4) | 4.24(4) | 5.28(5) |
| Tyr | — | — | — | — | .86(1) |

[a]24 hour hydrolysis in 6 N HCl.
[b]Average of hydrolysis at 24, 48, 72 hours in 6 N HCl/DMSO.
[c]Masked by cysteine oxidation product.
[d]Destroyed in course of hydrolysis.
[e]Determined by extrapolation to zero time of hydrolysis.
[f]Determined by extrapolation to 100 hours of hydrolysis.
[g]Determined as its cysteic acid derivative.
[h]21 hour hydrolysis in 6 N HCl.

J. Chemical Attachment of Peptides to KLH through SPDP.

The procedure described below for the smallest peptide studied was essentially the same for all peptides which were chemically bound to KLH. The maximum advisable loading level of SPDP [N-succinimidyl-3(2-pyridithio)propionate] to KLH was determined according to the extent of precipitation of the complex which occurred over a 60 minute reaction. It was observed that a 250 molar excess of SPDP to KLH was optimum. One-half gram of KLH ($\sim 1 \times 10^{-4}$ mmol) was dissolved in 25 ml of 0.1 M $Na_2HPO_4$, pH 7.2 with gentle sonication. A small quantity of insoluble material was removed by contrifugation, and to the supernatant was added 7.81 mg of SPDP ($2.5 \times 10^{-2}$ mmol) in 625 $\mu$l of DMF. After alkaline uptake ceased, the sample was centrifuged with the supernatant desalted by G-25 Sephadex chromatography, in 0.1 M $Na_2HPO_4$, pH 7.2 at 20 cm/hr. The loading level achieved in the derivatization was determined to be approximately 40% by DTT reduction.

To 100 mg of the functionalized KLH ($2 \times 10^{-6}$ mol of ligand) in 25 ml of 0.1 M $Na_2HPO_4$, pH 7.2, was added a ten-fold excess (44 mg, $2 \times 10^{-5}$ mol) of the (141–158)ProCysGly reduced peptide in 600 $\mu$l of 0.1 M Tris buffer at pH 7.4. The reaction was monitored by liberation of the ligand and found to be near quantitative in 60 minutes at 22° C. The sample was desalted on Sephacryl S-200 in 0.1 M $NH_4HCO_3$, pH 7.5, and lyophillized. The yields in coupling the 21-, 25-, and 38-residue peptides as based on limited reactant were, respectively, 84%, 85% and 68%.

K. Formulation of Peptides.

All peptides and peptide-KLH conjugates were dissolved in 10 mM Tris, pH 8.0, at the desired concentration and then diluted 1:1 with Freund's Complete adjuvant. The total volume as well as the antigen concentration administered to each animal is described for each experiment.

II. Biological Protocol

A. Guinea Pig Vaccination

Duncan Hartly closed colony random bred female guinea pigs, weighing 450–500 gms were used in all experiments. Each vaccine preparation was administered at the described dosage by subcutaneous injection in a volume of 0.15 ml to each member of a group of five guinea pigs. The only exception to the 0.15 ml total volume dosage was a 0.45 ml dose which was used in the antigen dose titration to deliver the highest concentration stated. The control vaccine was prepared from the $O_1$ Kaufbeuren strain, which was the one from which the published sequence data was derived. The vaccine was prepared with aluminium hydroxide gel and contained 1.66 mg of saponin per dose. Each of five guinea pigs was given one milliliter of vaccine by subcutaneous injection. The challenge virus was of the $O_1$ Kaufbeuren strain as described above. It was adapted to guinea pigs by serial passage of vesicular lymph and used for challenge purposes at the fifth guinea pig passage level. Following the virus titration, a 1/20 dilution was made to give a challenge dose of $10^{3.5}$ guinea pig $ID_{50}$, i.e., 3,000 infective doses per animal. All test animals were given the challenge virus by intradermal inoculation of the left hind foot pad—volume 0.02 ml. Each challenged guinea pig was observed for the subsequent 7 days for development of secondary or generalized lesions on the other hind foot or hands or mouth. The criterion of protection was the absence of any secondary lesions.

B. Cattle Vaccination

Six to eight month old heifers of mixed breeds weighing approximately 150–180 kg which were susceptible to foot and mouth disease were used in all experiments. Each vaccine preparation was administered at the described dosage by subcutaneous injection in a volume of 3 ml to each member of a group of three cattle. In each test a group of three cattle was non-vaccinated and served as positive experimental controls. All the animals were challenged by intradermolingual injection of $10^4$ ID$_{50}$ of freshly titrated O$_1$BFS 1860 virus in a 0.1 ml dose at ten sites on the tongue. Animals were examined daily post challenge for evidence of increase in body temperature and lesion development on the tongue and feet. Animals were deemed to be protected provided that no secondary lesions developed by seven days post-infection. All animal testing and sera evaluation was conducted at the Animal Viral Research Institute, United Kingdom.

C. Determination of Serum Neutralizing Titers (SNT)

The method employed for quantitation of serum neutralization titers was as described by Golding, S. M., Hedger, R. S., Talbot, T., Watson, J., *Research in Veterinary Science* 40, 142–147 (1976). All ELISA antibody titers are defined as directed against the peptide 140–160. Extremely close correlation of ELISA determinations and serum neutralization titers has been achieved in all vaccinations utilizing the described peptides.

III. Biological Results.

The most convincing method for establishing the relative potency of a series of potential synthetic peptide vaccines is to determine their minimum protective molar dose. Table 2 represents dose titration results obtained in guinea pigs with four differing immunogens. While the data is illuminating in several respects, the most important aspect is the marked enhancement in serum neutralizing titers (SNT) and protection achieved through the 38- and 40-residue peptides in comparison to that of the 21-residue peptide. Clearly these results indicate the unexpected advantageous properties of the compounds of this invention, which provide optimal protection upon viral challenge. The 38- and 40-residue peptides appear to be equivalent within experimental error and thereby minimize any importance of the amino terminal CysCys residues in the latter. These two peptides appear to confer complete protection at less than one-tenth to one-hundredth the dose of the 21-residue antigenic peptide. Of academic interest is the superiority of the free 21-residue peptide to its conjugate with keyhole limpet hemocyanin carrier (KLH) at an equivalent molar dose. This inhibition may be a functon of KLH purity, antigen concentration, and/or the differing methodology employed in conjugation, as others [Bittle et al, *Nature* 298, 30–33 (1982)], have reported success with a similar peptide. However, the unprecedented ability to protect guinea pigs against FMDV free of any stated carrier significantly simplifies the approach and eliminates a major source of variability. The most desirable synthetic agent capable of providing complete protection is that which encompasses the minimal viral structural information in a highly defined and pure state. The elimination of KLH or any like carrier as a necessity in providing protection marks a significant advance in the synthetic approach to vaccination.

TABLE 2

Dose Titration Comparison of Synthetic FMDV in Guinea Pigs

SNT O$_1$K:SNT O$_1$BFS[a] (No. protected:No. challenged)

| | Peptide Wt[b] | Volume[c] | 21-residue | 21-residue-KLH | 38-residue | 40-residue |
|---|---|---|---|---|---|---|
| 1. | 150 nmoles | 450 μl | 1/178:1/256(5:5) | 1/6:1/6(0:5) | 1/708:1/1024(5:5) | 1/4096:1/4096(5:5) |
| 2. | 50 nmoles | 150 μl | 1/6:1/32(1:5) | 1/6:1/6(0:5) | 1/1400:1/1400(5:5) | 1/1400:1/1400(5:5) |
| 3. | 17 nmoles | 150 μl | 1/8:1/6(2:5) | 1/6:1/6(0:5) | 1/1024:1/1400(5:5) | 1/1400:1/2048(5:5) |
| 4. | 6 nmoles | 150 μl | 1/6:1/6(0:5) | 1/6:1/6(0:5) | 1/708:1/708(4:4) | 1/128:1/90(5:5) |
| 5. | 2 nmoles | 150 μl | 1/6:1/6(0:5) | 1/6:1/6(0:5) | 1/128:1/256(3:4) | 1/178:1/64(4:5) |
| 6. | 0.6 nmoles | 150 μl | 1/6:1/6(0:5) | 1/6:1/6(0:5) | 1/11:1/90(5:5) | 1/128:1/178(3:5) |
| 7. | 0.2 nmoles | 150 μl | 1/6:1/6(0:5) | 1/6:1/6(0:5) | 1/16:1/22(1:5) | 1/64:1/22(1:5) |

[a]Determined at 28 days after vaccination in pooled sera of all animals immunized with indicated peptide.
[b]Peptide weight for 21-residue-KLH is expressed as the amount of the synthetic peptide present in the conjugate.
[c]One-half of the volume consisted of Complete Freund's adjuvant.

The necessity of antigen optimization is of utmost importance, as commercialization will quite likely warrant utilization of an adjuvant of lesser potency than Complete Freunds. Table 3 reveals that at a molar dose comparable to that which provided protection with the 21-residue peptide in Complete Freunds adjuvant, the 40-residue peptide was completely protective with a commercially acceptable Al(OH)$_3$ adjuvant. The absolute weight of antigen providing full protection of guinea pigs with the latter adjuvant, in a single vaccination, is less than 1 mg.

TABLE 3

Adjuvant Evaluation in Guinea Pigs with 40-Residue Peptide Vaccination

| Peptide Conc | Adjuvant | No. Protected/No. Challenged |
|---|---|---|
| 150 nmoles | Freunds Complete | 5/5 |
| 17 nmoles | " | 5/5 |
| 2 nmoles | " | 4/5 |
| 0.2 nmoles | " | 0/5 |
| 150 nmoles | Al(OH)$_3$ | 5/5 |
| 17 nmoles | " | 1/5 |
| 2 nmoles | " | 0/5 |
| 0.2 nmoles | " | 0/4 |

A variety of synthetic peptides were evaluated to determine their effect in guinea pigs. The data, provided in Table 4, establish the clear and unexpected superiority of compounds of this invention when compared with other shorter and longer sequences not within the scope of this invention.

TABLE 4

Guinea Pigs Vaccinated with a Variety of Peptides

No. of Guinea Pigs Protected/No. Vaccinated
Amount of Peptide, nmoles

| Peptide[a] | 125 | 25 | 5 | 1 |
|---|---|---|---|---|
| A | 0/4 | 0/4 | 0/4 | 0/4 |
| B | 3/4 | 0/4 | 0/4 | 0/4 |
| C | 4/4 | 3/4 | 0/3 | 0/4 |
| D | 4/4 | 3/4 | 0/3 | 0/4 |
| E | 0/4 | 0/4 | 0/3 | 0/4 |
| F | 1/4 | 0/4 | 0/4 | 0/4 |
| G | 2/4 | 2/4 | 1/4 | 0/4 |

[a]A - O$_1$K Sequence 200–213.
B - O$_1$K Sequence 134–160.
C - 40 Residue Peptide.
D - 45 Residue Peptide.
E - O$_1$K Sequence 161–213.
F - O$_1$K Sequence 134–213.
G - Mixture of O$_1$K Sequence 200–213 and O$_1$K Sequence 134–160.

While guinea pigs have proven to be a useful model for evaluation of FMD vaccines, the ultimate test of success must be in cattle, the principal commercial target animal. Table 5 represents the results of cattle vaccination, with the 40-residue peptide, followed by the conventional challenge consisting of direct viral infection of the tongue in each vaccinated animal. The serum neutralization titers increased rapidly to reach a near maxima at Day 14, which was maintained at least through the time of challenge (Day 32). Two of the nine animals which were challenged on Day 32 were completely protected, having exhibited no signs of secondary lesions. These animals represent the first example of successful single cattle vaccination for FMD with a synthetic peptide and thereby attest to the potency of the immunogens of this invention. Furthermore, by serological determination of the neutralization antibody concentrations immediately prior to challenge it is not possible to predict protection. In comparison to the known minimum levels of neutralizing antibody concentrations required by a conventional FMD vaccine all of these animals should have been clearly protected. Consequently, at this time it is not acceptable to establish the efficacy of a peptide vaccine on the comparative basis of its SNT value with a conventional vaccine. Reimmunization of animals 1, 2, and 3 led to complete protection after an additional 14 days prior to challenge. Antibody titers in these animals as measured by ELISA were observed to increase approximately one half of a log unit following booster immunization. This 40-residue peptide is less than one-fifth the size of any other synthetic antigen which has proven capable of cattle protection. Its synthetic nature will allow evaluation of its inherent activity in combination with various adjuvants, free of any potential low level bacterial potentiation.

serotypes and the other of which contains from 14 to 20 amino acid residues and includes the amino acid residue sequence in positions 200 to 213 of the O serotype or the equivalent sequence of other serotypes;

X is H, H-Cys, or H-Cys-Cys, the sulfhydryls of which may be blocked or free;

Z is OH, Cys-OH, or Pro-Cys-Gly-OH, the sulfhydryls of which may be blocked or free; and Y is a sequence of from about 2 to about 6 amino acid residues.

2. Compound of claim 1, in which X is hydrogen.

3. Compound of claim 2, in which Z is Pro-Cys-Gly-OH.

4. Compound of claim 2, in which Z is Cys-OH.

5. Compound of claim 2, in which Z is OH.

6. Compound of claim 2, in which Y contains the dipeptide sequence -Pro-Pro-.

7. Compound of claim 6, in which Y is a sequence of from about 2 to about 4 amino acids.

8. Compound of claim 7, in which Y is -Pro-Pro-.

9. Compound of claim 7, in which Y is -Pro-Pro-Ser-.

10. Compound of claim 2, in which A and B are peptide sequences derived from the same serotype.

11. Compound of claim 10, in which one of A or B is the amino acid residue sequence in positions 200 to 213 of the O serotype or the equivalent sequence of other serotypes.

12. Compound of claim 11, in which one of A or B is the amino acid residue sequence in positions 141 to 158 of the O serotype or the equivalent sequence of other serotypes.

13. Compound of claim 10, in which A is the amino acid residue sequence in positions 200 to 213 of the O serotype or the equivalent sequence of other serotypes

TABLE 5

Evaluation of Synthetic FMD Vaccine in Cattle

| Animal No. | Peptide wt.[a] | SNT-Days Post Vaccination | | | | | Challenge Result[b] |
| --- | --- | --- | --- | --- | --- | --- | --- |
| | | 0 | 7 | 14 | 21 | 26 | 32 | |
| 1. | 1 mg | 1/6 | 1/16 | 1/708 | 1/1024 | 1/1024 | 1/≧1400 | Protected |
| 2. | " | 1/22 | 1/22 | 1/≧1400 | 1/≧1400 | 1/≧1400 | 1/≧1400 | " |
| 3. | " | 1/16 | 1/45 | 1/1024 | 1/1024 | 1/1024 | 1/1024 | " |
| 4. | 0.2 mg | 1/11 | 1/22 | 1/≧1400 | 1/≧1400 | 1/1024 | 1/≧1400 | Not Protected |
| 5. | " | 1/6 | 1/22 | 1/≧1400 | 1/≧1400 | 1/≧1400 | 1/≧1400 | " |
| 6. | " | 1/32 | 1/32 | 1/≧1400 | 1/≧1400 | 1/≧1400 | 1/1024 | " |
| 7. | 1.0 mg | 1/8 | 1/11 | 1/355 | 1/256 | 1/355 | 1/512 | " |
| 8. | " | 1/32 | 1/22 | 1/≧1400 | 1/≧1400 | 1/1024 | 1/1024 | " |
| 9. | " | 1/11 | 1/22 | 1/1024 | 1/708 | 1/1024 | 1/1024 | " |
| 10. | 5.0 mg | 1/6 | 1/45 | 1/1024 | 1/≧1400 | 1/≧1400 | 1/≧1400 | Protected |
| 11. | " | 1/6 | 1/16 | 1/≧1400 | 1/≧1400 | 1/≧1400 | 1/≧1400 | " |
| 12. | " | 1/11 | 1/22 | 1/355 | 1/512 | 1/≧1400 | 1/1024 | Not Protected |
| 13. | None | 1/6 | 1/16 | 1/11 | 1/6 | 1/90 | 1/32 | " |
| 14. | " | 1/11 | 1/11 | 1/11 | 1/11 | 1/11 | 1/22 | " |
| 15. | " | 1/11 | 1/8 | 1/11 | 1/8 | 1/11 | 1/16 | " |
| 16. | " | 1/11 | 1/6 | 1/11 | 1/6 | 1/11 | 1/11 | " |

[a]Peptide administered was CysCys[(200-213)ProProSer(141-158)]ProCysGly as a 3 ml aqueous buffered suspension containing 50% Freunds Complete adjuvant.
[b]Animals 4-16 were challenged on Day 32 following SNT determination, while the first three animals were revaccinated on Day 38 with 0.2 mg of peptide in a 3 ml suspension of Freunds Incomplete adjuvant and challenged on Day 52.

We claim:

1. A compound capable of eliciting a neutralization response against foot-and-mouth disease virus containing a sequence of the formula

X-A-Y-B-Z in which A and B are amino acid residue sequences comprising sequences of the foot-and-mouth disease virus $VP_1$ capsid protein serotypes, one of which contains from 18 to 24 amino acid residues and includes the amino acid residue sequence in positions 141 to 158 of the O serotype or the equivalent sequence of other and B is the amino acid residue sequence in positions 141 to 158 of the O serotype or the equivalent sequence of other serotypes.

14. Compound of claim 10, in which A is the amino acid residue sequence in positions 141 to 158 of the O serotype or the equivalent sequence of other serotypes and B is the amino acid residue sequence in positions 200 to 213 of the O serotype or the equivalent sequence of other serotypes.

15. Compound of claim 13, in which Z is Pro-Cys-Gly-OH.

16. Compound of claim 15, in which Y contains the dipeptide sequence -Pro-Pro-.

17. Compound of claim 16, in which Y is -Pro-Pro-Ser-.

18. Compound of claim 5, in which X is H-Cys.

19. Compound of claim 18, in which Y is -Leu-Pro-Pro-Thr-.

20. Compound of claim 19, in which A is the amino acid residue sequence -Arg-Tyr-Asn-Arg-Asn-Ala(1-41-158) in which (141-158) is the amino acid residue sequence in positions 141 to 158 of the O serotype.

21. Compound of claim 20, in which B is the amino acid residue sequence -Glu-Ala-(200-213) in which (200-213) is the amino acid residue sequence in positions 200-213 of the O serotype.

* * * * *